US009517994B2

(12) United States Patent
Ebright et al.

(10) Patent No.: US 9,517,994 B2
(45) Date of Patent: Dec. 13, 2016

(54) ANTIBACTERIAL AGENTS: PHLOROGLUCINOL DERIVATIVES

(71) Applicant: Rutgers, the State University of New Jersey, New Brunswick, NJ (US)

(72) Inventors: Richard H. Ebright, New Brunswick, NJ (US); Juan Shen, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/370,395

(22) PCT Filed: Jan. 7, 2013

(86) PCT No.: PCT/US2013/020545
§ 371 (c)(1),
(2) Date: Jul. 2, 2014

(87) PCT Pub. No.: WO2013/103969
PCT Pub. Date: Jul. 11, 2013

(65) Prior Publication Data
US 2015/0011647 A1 Jan. 8, 2015

Related U.S. Application Data

(60) Provisional application No. 61/583,444, filed on Jan. 5, 2012.

(51) Int. Cl.
C07C 49/84 (2006.01)
C07C 49/83 (2006.01)
C07C 49/825 (2006.01)

(52) U.S. Cl.
CPC ............ *C07C 49/84* (2013.01); *C07C 49/825* (2013.01); *C07C 49/83* (2013.01)

(58) Field of Classification Search
CPC ........... A61K 31/12; A61K 8/35; C07C 49/84; C07C 45/46; A01N 35/04
USPC .......................................... 514/685; 568/331
See application file for complete search history.

(56) References Cited

U.S. PATENT DOCUMENTS

| | | | |
|---|---|---|---|
| 2,898,374 A | 8/1959 | Riedl | |
| 4,061,769 A | 12/1977 | Ohno et al. | |
| 4,421,763 A | 12/1983 | Hamano et al. | |
| 5,411,728 A | 5/1995 | Joulain et al. | |
| 6,022,983 A | 2/2000 | Wuonola et al. | |
| 6,169,181 B1 | 1/2001 | Romines et al. | |
| 6,191,288 B1 | 2/2001 | Ramamoorthy | |
| 6,228,882 B1 | 5/2001 | Wuonola et al. | |
| 8,114,583 B2 | 2/2012 | Ebright | |
| 8,772,332 B2 | 7/2014 | Ebright | |
| 2003/0065039 A1* | 4/2003 | Kharazmi et al. | 514/678 |
| 2005/0187170 A1 | 8/2005 | Bantia et al. | |
| 2006/0100291 A1 | 5/2006 | Perry et al. | |
| 2007/0292355 A1 | 12/2007 | Tamarkin et al. | |
| 2013/0237595 A1 | 9/2013 | Ebright et al. | |
| 2013/0289128 A1 | 10/2013 | Ebright et al. | |
| 2015/0031640 A1 | 1/2015 | Ebright | |
| 2015/0051275 A1 | 2/2015 | Ebright et al. | |

FOREIGN PATENT DOCUMENTS

| | | |
|---|---|---|
| WO | WO 2007/094799 | 8/2007 |
| WO | WO 2012/033846 | 3/2012 |
| WO | WO 2012/037508 | 3/2012 |
| WO | WO 2013/119564 | 8/2013 |
| WO | WO 2013/142812 | 9/2013 |
| WO | WO 2013/192352 | 12/2013 |

OTHER PUBLICATIONS

Werner, S., H. Chen, H. Jiang, J. Morgan "Synthesis of non-natural flavanones and dihydrochalcones in metabolically engineered yeast", Journal of Molecular Catalysis B: Enzymatic (2010), 66 (3-4), pp. 257-263.*

Iinuma, M., T. Tanaka, M. Mizuno, T. Katsuzaki, and H. Ogawa "Structure-Activity Correlation of Flavanoids for Inhibition of Bovine Lens Aldose Reductase" Chem. Pharm. Bull. (1989), 37 (7), pp. 1813-1815.*

Mapunya, M., A. Hussein, B. Rodriguez, and N. Lall "Tyrosinase activity of Greyia flanaganii (Bolus) constituents" Phytomedicine (2011), 18, pp. 1006-1012.*

Andre et al. "Novel synthetic molecules targeting the bacterial RNA polymerase assembly", *Journal of Antimicrobial Chemotherapy*, 57, 245-251 (2006).

Chatterjee et al., "Isolation and structure of archangelenone. Flavonoid constituent of Angelica archangelica", XP002692911, Database Caplus [Online] Chemical Abstracts accession No. 1973:489536.

(Continued)

*Primary Examiner* — Sagar Patel

(74) *Attorney, Agent, or Firm* — Viksnins Harris & Padys PLLP

(57) ABSTRACT

The invention provides a compound of formula I:

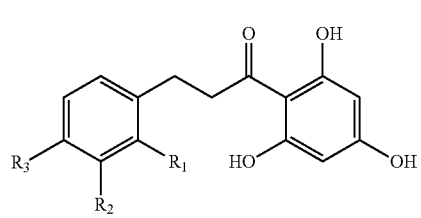

or a salt thereof, wherein $R_1$-$R_3$ have any of the values described in the specification, as well as compositions comprising a compound of formula I. The compounds are useful as antibacterial agents.

14 Claims, No Drawings

(56) References Cited

OTHER PUBLICATIONS

Doundoulakis et al., "Myxopyronin B analogs as inhibitors of RNA polymerase, synthesis and biological evaluation", *Bioorganic & Medicinal Chemistry Letters 14*, 5667-5672 (2004).
Doundoulakis et al., "Myxopyronin B analogs as inhibitors of RNA polymerase, synthesis and biological evaluation", HCAPLUS Accession No. 2004:863124, 5 pages, Bioorganic & Medicinal Chemistry Letters, 14(22), 5667-5672 (2004).
Hu, "Total syntheses of biologically active natural products: motuporin, oleandolide, (±)-myxopyronin A and B", HCAPLUS Accession No. 2000:514322, 1 page, Diss. Abstr. Int., B 2000, 60(10), 5094.
Lira et al., "Syntheses of novel myxopyronin B analogs as potential inhibitors of bacterial RNA polymerase", *Bioorganic & Medicinal Chemistry Letters 17*, 6797-6800 (2007).
Mukhopadhyay et al., "The RNA Polymerase "Switch Region" is a Target for Inhibitors", *Cell 135*, 295-307 (2008).
Mukhopadhyay et al., "The RNA polymerase "switch region" is a target for inhbitiors" HCAPLUS Accession No. 2008:1312023, 2 pages, Cell 135(2), 295-307 (2008).
Patent Cooperation Treaty, International Searching Authority, Search Report and Written Opinion for PCT/US2013/020545, 12 pages, Apr. 18, 2013.
Srivastava et al., "New Target for inhibition of bacterial RNA polymerase: switch region", *Curr. Opini. Microbiol. 14*, 532-563 (2011).
U.S. Appl. No. 14/409,407.

* cited by examiner

ANTIBACTERIAL AGENTS: PHLOROGLUCINOL DERIVATIVES

CROSS-REFERENCE TO RELATED APPLICATION(S)

This patent application claims the benefit of priority of U.S. application Ser. No. 61/583,444, filed Jan. 5, 2012, which application is herein incorporated by reference.

GOVERNMENT FUNDING

The invention described herein was made with United States Government support under Grant Numbers AI072766 and AI090837 awarded by the National Institutes of Health. The United States Government has certain rights in the invention.

BACKGROUND OF THE INVENTION

The emergence of drug-resistant and multidrug-resistant (MDR) bacterial pathogens (e.g., methicillin-resistant *Staphylococcus aureus*, MRSA) has increased concerns as to the adequacy of current antimicrobials and pathogen treatment methods. The lethality of such pathogens has often led to treatment methods that are experimental or would otherwise normally be avoided in standard clinical practice. For example, the antibiotic colistin was traditionally considered too nephrotoxic and neurotoxic for clinical use, but is nevertheless used to treat MDR bacterial infections due to a paucity of available active drugs. The growing threat from MDR pathogens highlights a critical need for new antibiotics, e.g., antibiotics that exhibit novel mechanisms of action and/or that are able to circumvent known resistance pathways.

SUMMARY OF THE INVENTION

Applicant has identified compounds that inhibit bacterial RNA polymerase and inhibit bacterial growth. Accordingly, in one embodiment the invention provides a compound of formula I:

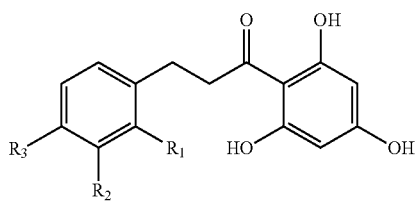

wherein:
$R_1$ is H, Cl, Br, I, $(C_1-C_6)$alkyl, optionally substituted by halogen, or $(C_1-C_6)$alkoxy, optionally substituted by halogen;
$R_2$ is H, halogen, trifluoromethyl, $(C_2-C_6)$alkyl, optionally substituted by halogen, or $(C_1-C_6)$alkoxy, optionally substituted by halogen;
$R_3$ is H, halogen, trifluoromethyl, $(C_2-C_6)$alkyl, optionally substituted by halogen, or $(C_2-C_6)$alkoxy, optionally substituted by halogen;
provided that at least one of $R_1$, $R_2$, or $R_3$ is not H;
or a salt thereof.

In certain embodiments, the compound is OMTK11, OMTK12, OMTK13, OMTK14, OMTK15, OMTK18, OMTK21, OMTK22, OMTK23, OMTK26, OMTK27, OMTK28, OMTK30, OMTK31, or OMTK32

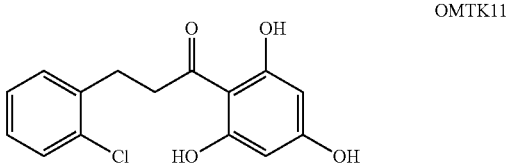
OMTK11

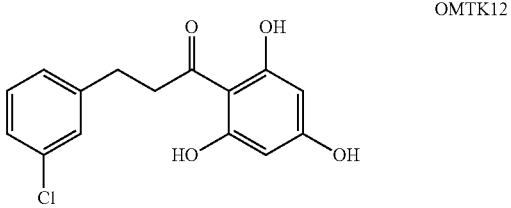
OMTK12

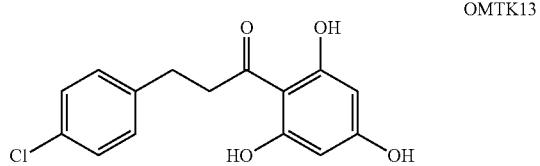
OMTK13

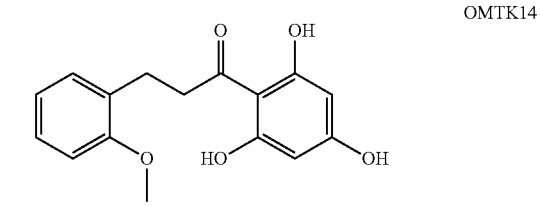
OMTK14

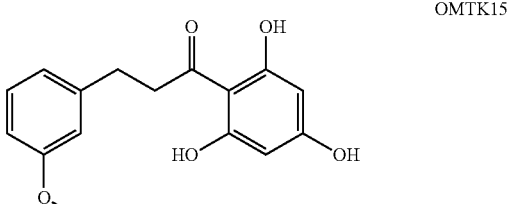
OMTK15

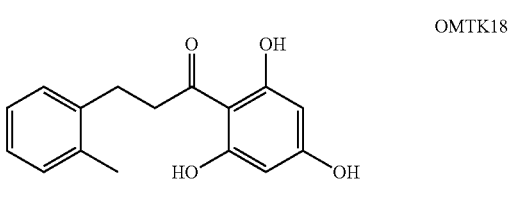
OMTK18

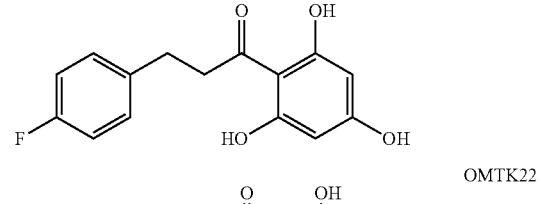
OMTK21

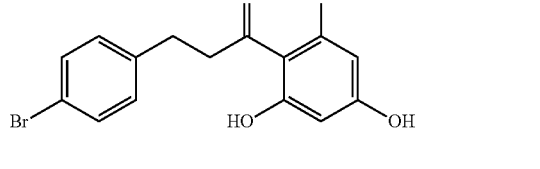
OMTK22

-continued

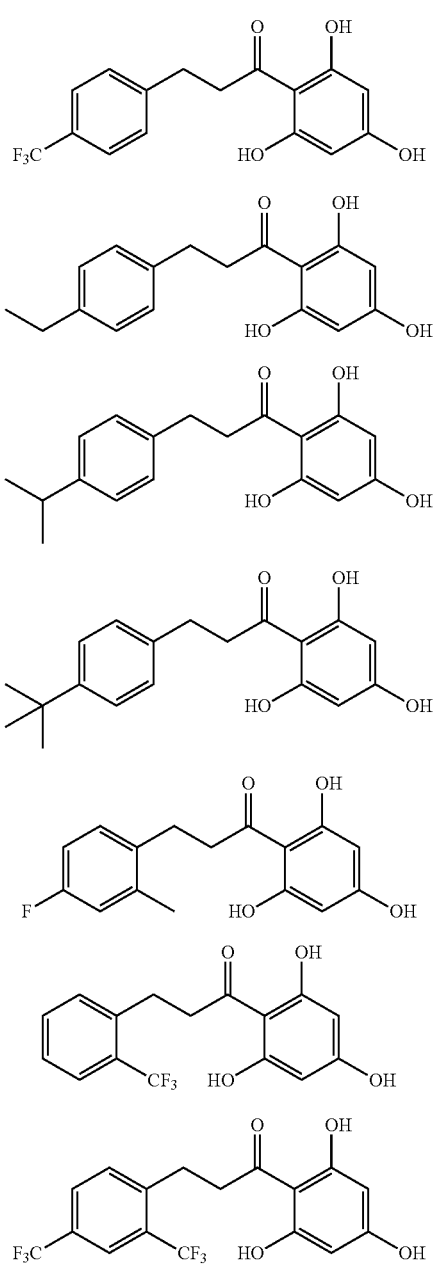

OMTK23
OMTK26
OMTK27
OMTK28
OMTK30
OMTK31
OMTK32 or a salt thereof.

The invention also provides a composition comprising a compound of formula I, or a pharmaceutically acceptable salt thereof, and a pharmaceutically acceptable vehicle.

The invention also provides a method for inhibiting a bacterial RNA polymerase comprising contacting the bacterial RNA polymerase with a compound of formula I, or a salt thereof.

The invention also provides a method for inhibiting the growth of a bacteria comprising contacting the bacteria with a compound of formula I or a salt thereof.

The invention also provides a method for treating a bacterial infection in a mammal comprising administering to the mammal an effective amount of a compound of formula I or a pharmaceutically acceptable salt thereof.

The invention also provides a compound of formula I or a pharmaceutically acceptable salt thereof for use in the prophylactic or therapeutic treatment of a bacterial infection.

The invention also provides a compound of formula I or a pharmaceutically acceptable salt thereof for use in medical treatment.

The invention also provides the use of a compound of formula I or a pharmaceutically acceptable salt thereof for the preparation of a medicament for treating a bacterial infection in a mammal. The invention also provides the use of a compound of formula I or a salt thereof as a disinfectant, sterilant, antispoilant, or antiseptic.

In certain embodiments, the bacteria is selected from *Mycobacterium tuberculosis, Staphylococcus aureus* MSSA and MRSA, *Enterococcus faecalis, Enterococcus faecium, Bacillus anthracia, Escherichia coli, Haemophilus influenzae, Moraxella catarrhalis, Francisella tularensis*, and *Burkholderia mallei*.

The invention also provides synthetic processes and intermediates disclosed herein that are useful for preparing compounds of formula (I) or salts thereof.

The invention provides new compounds and compositions that inhibit bacterial RNA polymerase and inhibit bacterial growth. The compounds will have applications in analysis of RNA polymerase structure and function, control of bacterial gene expression, control of bacterial growth, antibacterial chemistry, antibacterial therapy, and drug discovery.

DETAILED DESCRIPTION

The following definitions are used, unless otherwise described. Halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active, and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

It will also be appreciated that compounds of the invention can exist in different tautomeric forms. The compounds of formula I also encompasses any tautomeric forms or mixtures thereof.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl.

Specifically, $(C_1-C_6)$alkoxy can be methoxy, ethoxy, propoxy, isopropoxy, butoxy, iso-butoxy, sec-butoxy, pentoxy, 3-pentoxy, or hexyloxy.

Processes for preparing compounds of formula I are provided as further embodiments of the invention.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, e.g., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula Ito the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 125 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to inhibit bacterial RNA polymerase can be determined using biochemical models that are well known to the art, or as described in the Examples.

The ability of a compound of the invention to inhibit bacterial growth in culture can be determined using biochemical models that are well known to the art, or as described in the Examples.

The invention will now be illustrated by the following non-limiting Examples. As illustrated by the Examples and Table 1, compounds of formula I have been synthesized and demonstrated to inhibit bacterial RNA polymerase and inhibit bacterial growth.

EXAMPLES

Example 1

Synthesis of
3-(2-chlorophenyl)propanoyl-phloroglucinol (1;
0MTK11)

Phloroglucinol (1.26 g, 10 mmol, Aldrich), 3-(2-chlorophenyl)propionic acid (1.84 g; 10 mmol; Alfa Aesar), and anhydrous $AlCl_3$ (5.00 g; 37.5 mmol; Aldrich) were added to a flame-dried 100 ml round-bottom flask. $POCl_3$ (25.15 g; 15 ml; 164 mmol, Aldrich) was added at 0° C. The reaction mixture was stirred under $N_2$ for 2 h at 0° C. and 8 h at room temperature and then was poured into crushed ice (100 g) and extracted with ethyl acetate (3×100 ml). The organic layer was dried over anhydrous $Na_2SO_4$ and evaporated under vacuum to yield an oily residue. Product 1 was isolated by chromatography on silica gel. Yield: 40%. MS (MALDI): calculated, m/z 293.1 ($MH^+$; found, 293.1.

Example 2

Synthesis of
3-(3-chlorophenyl)propanoyl-phloroglucinol (2;
0MTK12)

3-(3-chlorophenyl)propanoyl-phloroglucinol (2) was synthesized as described in Example 1, using 3-(3-chlorophenyl)propionic acid (1.84 g; 10 mmol; Aldrich) in place of 3-(2-chlorophenyl)propionic acid. Overall yield: 42%. MS (MALDI): calculated, m/z 293.1 ($MH^+$); found, 293.1.

Example 3

Synthesis of
3-(4-chlorophenyl)propanoyl-phloroglucinol (3;
0MTK13)

3-(4-chlorophenyl)propanoyl-phloroglucinol (3) was synthesized as described in Example 1, using 3-(4-chlorophenyl)propionic acid (1.84 g; 10 mmol; Aldrich) in place of 3-(2-chlorophenyl)propionic acid. Overall yield: 38%. MS (MALDI): calculated, m/z 293.1 ($MH^+$); found, 293.1.

Example 4

Synthesis of
3-(2-methoxyphenyl)propanoyl-phloroglucinol (4;
0MTK14)

3-(2-methoxyphenyl)propanoyl-phloroglucinol (4) was synthesized as described in Example 1, using 3-(2-methoxyphenyl)propionic acid (1.80 g; 10 mmol; Aldrich) in place of 3-(2-chlorophenyl)propionic acid. Overall yield: 41%. MS (MALDI): calculated, m/z 289.1 ($MH^+$); found, 289.1.

Example 5

Synthesis of
3-(3-methoxyphenyl)propanoyl-phloroglucinol (5;
0MTK15)

3-(3-methoxyphenyl)propanoyl-phloroglucinol (5) was synthesized as described in Example 1, using 3-(3-methoxyphenyl)propionic acid (1.80 g; 10 mmol; Aldrich) in place of 3-(2-chlorophenyl)propionic acid. Overall yield: 39%. MS (MALDI): calculated, m/z 289.1 ($MH^+$); found, 289.1.

Example 6

Synthesis of
3-(2-methylphenyl)propanoyl-phloroglucinol (6;
0MTK18)

3-(2-methylphenyl)propanoyl-phloroglucinol (6) was synthesized as described in Example 1, using 3-(2-methylphenyl)propionic acid (1.64 g; 10 mmol; Aldrich) in place of 3-(2-chlorophenyl)propionic acid. Overall yield: 45%. MS (MALDI): calculated, m/z 273.1 (MH$^+$); found, 273.1.

Example 7

Synthesis of 3-(4-fluorophenyl)propanoyl-phloroglucinol (7; OMTK21)

3-(4-fluorophenyl)propanoyl-phloroglucinol (7) was synthesized as described in Example 1, using 3-(4-fluorophenyl)propionic acid (1.68 g; 10 mmol; Aldrich) in place of 3-(2-chlorophenyl)propionic. Overall yield: 42%. MS (MALDI): calculated, m/z 277.1 (MH$^+$); found, 277.1.

Example 8

Synthesis of 3-(4-bromophenyl)propanoyl-phloroglucinol (8; OMTK22)

3-(4-bromophenyl)propanoyl-phloroglucinol (8) was synthesized as described in Example 1, using 3-(4-bromophenyl)propionic acid (2.29 g; 10 mmol; Aldrich) in place of 3-(2-chlorophenyl)propionic acid. Overall yield: 40%. MS (MALDI): calculated, m/z 337.0 (MH$^{30}$); found, 337.1.

Example 9

Synthesis of 3-(4-trifluoromethylphenyl)propanoyl-phloroglucinol (9; OMTK23)

3-(4-trifluoromethylphenyl)propanoyl-phloroglucinol (9) was synthesized as described in Example 1, using 3-(4-trifluoromethylphenyl)propionic acid (2.18 g; 10 mmol; Aldrich) in place of 3-(2-chlorophenyl)propionic acid. Overall yield: 42%. MS (MALDI): calculated, m/z 327.1 (MH$^+$); found, 327.1.

Example 10

Synthesis of 3-(4-ethylphenyl)propanoyl-phloroglucinol (10; OMTK26)

3-(4-ethyllphenyl)propanoyl-phloroglucinol (10) was synthesized as described in Example 1, using 3-(4-ethylphenyl)propionic acid (1.78 g; 10 mmol; Aldrich) in place of 3-(2-chlorophenyl)propionic acid. Overall yield: 40%. MS (MALDI): calculated, m/z 287.1 (MH$^+$); found, 287.1.

Example 11

Synthesis of 3-(4-isopropylphenyl)propanoyl-phloroglucinol (11; OMTK27)

3-(4-isopropylphenyl)propanoyl-phloroglucinol (11) was synthesized as described in Example 1, using 3-(4-isopropylphenyl)propionic acid (1.92 g; 10 mmol; Aldrich) in place of 3-(2-chlorophenyl)propionic acid. Overall yield: 42%. MS (MALDI): calculated, m/z 301.1 (MH$^+$); found, 301.1.

Example 12

Synthesis of 3-((4-tert-butyl)phenyl)propanoyl-phloroglucinol (12; OMTK28)

3-((4-tert-butyl)phenyl)propanoyl-phloroglucinol (12) was synthesized as described in Example 1, using 3-((4-tert-butyl)phenyl)propionic acid (2.06 g; 10 mmol; Aldrich) in place of 3-(2-chlorophenyl)propionic acid. Overall yield: 38%. MS (MALDI): calculated, m/z 315.2 (MH$^+$); found, 315.2.

Example 13

Synthesis of 3-(4-fluoro-2-methylphenyl)propanoyl-phloroglucinol (13; OMTK30)

3-(4-fluoro-2-methylphenyl)propanoyl-phloroglucinol (13) was synthesized as described in Example 1, using 3-(4-fluoro-2-methylphenyl)propionic acid (1.82 g; 10 mmol; Aldrich) in place of 3-(2-chlorophenyl)propionic acid. Overall yield: 41%. MS (MALDI): calculated, m/z 291.1 (MH$^+$); found, 291.1.

Example 14

Synthesis of 3-(2-(trifluoromethyl)phenyl)propanoyl-phlorogiucinol (14; OMTK31)

3-(2-(trifluoromethyl)phenyl)propanoyl-phloroglucinol (14) was synthesized as described in Example 1, using 3-(2-(trifluoromethyl)phenyl)propionic acid (2.18 g; 10 mmol; Aldrich) in place of 3-(2-chlorophenyl)propionic acid. Overall yield: 39%. MS (MALDI): calculated, m/z 327.1 (MH$^+$); found, 327.1.

Example 15

Synthesis of 3-(2,4-bis(trifluoromethyl)phenyl)propanoyl-phloroglucinol (15; OMTK32)

3-(2,4-bis(trifluoromethyl)phenyl)propanoyl-phloroglucinol (15) was synthesized as described in Example 1, using 3-(2,4-bis(trifluoromethyl)phenyl)propionic acid (2.86 g; 10 mmol; Aldrich) in place of 3-(2-chlorophenyl)propionic acid. Overall yield: 45%. MS (MALDI): calculated, m/z 395.1 (MH$^+$); found, 395.1.

Example 16

Synthesis of 3-(2,4-dimethoxyphenyl)propanoyl-phloroglucinol (16; OMTK33)

3-(2,4-dimethoxyphenyl)propanoyl-phloroglucinol (16) was synthesized as described in Example 1, using 3,4-dimethoxyphenylacetic acid (1.96 g; 10 mmol; Aldrich) in place of 3-(2-chlorophenyl)propionic acid. Yield: 15%. MS (MALDI): calculated, m/z 305.1 (MH+); found, 305.1.

Example 17

Assay of Inhibition of Bacterial RNA Polymerase

Example 17.1

Assay of Inhibition of *Escherichia coli* RNA Polymerase

Fluorescence-detected RNA polymerase assays with *E. coli* RNA polymerase were performed by a modification of the procedure of Kuhlman et al., 2004 (Kuhlman, P., Duff, H. & Galant, A. (2004) *Anal. Biochem.* 324, 183-190). Reaction mixtures contained (20 μl): 0-100 nM test compound, 75 nM *E. coli* RNA polymerase $\sigma^{70}$ holoenzyme, 20 nM 384 by DNA fragment containing the bacteriophage T4 N25 promoter, 100 μM ATP, 100 μM GTP, 100 μM UTP, 100 μM CTP, 50 mM Tris-HCl, pH 8.0, 100 mM KCl, 10 mM $MgCl_2$, 1 mM DTT, 10 μg/ml bovine serum albumin, and 5.5% glycerol. Reaction components other than DNA and NTPs were pre-incubated for 10 mm at 37° C. Reactions were carried out by addition of DNA and incubation for 5 min at 37° C., followed by addition of NTPs and incubation for 60 min at 37° C. DNA was removed by addition of 1 μl 5 mM $CaCl_2$ and 2 U DNaseI (Ambion, Inc.), followed by incubation for 90 min at 37° C. RNA was quantified by addition of 100 μl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QMI spectrofluorometer (PTI, Inc.)]. IC50 was defined as the concentration of inhibitor resulting in 50% inhibition of RNA polymerase activity.

Example 17.2

Assay of Inhibition of *Mycobacterium tuberculosis* RNA Polymerase

Fluorescence-detected RNA polymerase assays with M tuberculosis RNA polymerase were performed as in Example 17.1, using reaction mixtures containing (20 μl): 0-100 nM test compound, 75 nM M tuberculosis RNA polymerase core enzyme, 300 nM *M. tuberculosis* $\sigma^4$, 20 nM 384 by DNA fragment containing the bacteriophage T4 N25 promoter, 100 μM ATP, 100 μM GTP, 100 μM UTP, 100 μM CTP, 40 mM Tris-HCl, pH 8.0, 80 mM NaCl, 5 mM $MgCl_2$, 2.5 mM DTT, and 12.7% glycerol. IC50 was defined as the concentration of inhibitor resulting in 50% inhibition of RNA polymerase activity.

Example 17.3

Assay of Inhibition of *Staphylococcus aureus* RNA Polymerase

Fluorescence-detected RNA polymerase assays with *S. aureus* RNA polymerase were performed as in Example 17.1, using reaction mixtures containing (20 μl): 0-100 nM test compound, 75 nM *S. aureus* RNA polymerase core enzyme, 300 nM *S. aureus* $\sigma^4$, 20 nM 384 by DNA fragment containing the bacteriophage T4 N25 promoter, 100 μM ATP, 100 μM GTP, 100 μM UTP, 100 μM CTP, 40 mM Tris-HCl, pH 8.0, 80 mM NaCl, 5 mM $MgCl_2$, 2.5 mM DTT, and 12.7% glycerol. IC50 was defined as the concentration of inhibitor resulting in 50% inhibition of RNA polymerase activity.

Example 18

Assay of Inhibition of Bacterial Growth in Culture

Example 18.1

Assay of Inhibition of Growth of *Staphylococcus aureus, Enterococcus faecalis*, and *Escherichia coli*

Minimum inhibitory concentrations (MICs) for Staphylococcus aureus ATCC 12600, Enterococcus faecalis ATCC 19433, and *Escherichia coli* D21f2tolC were quantified using, spiral gradient endpoint assays, essentially as described (Wallace, A. and Corkill, J. (1989) *J. Microbiol. Meths.* 10, 303-310; Paton, J., Holt, A., and Bywater, M. (1990) *Int. J Exp. Clin. Chemother.* 3, 31-38; Schalkowsky S. (1994) *Adv. Exp. Med. Biol.* 349, 107-120). Assays employed exponential-gradient plates containing 150 mm×4 mm Mueller-Hinton II cation-adjusted agar and 0.4-100 μg/ml of test compound. Plates were prepared using an Autoplate 4000 spiral plater (Spiral Biotech, Inc.). Saturated overnight cultures were swabbed radially onto plates, and plates were incubated for 16 h at 37° C. For each culture, the streak length was measured using a clear plastic template (Spiral Biotech, Inc.), the test-compound concentration at the streak endpoint was calculated using the program SGE (Spiral Biotech, Inc.), and the MIC was defined as the calculated test-compound concentration at the streak endpoint.

Example 18.2

Assay of Inhibition of Growth of *Haemophilus influenzae* and *Moraxella catarrhalis*

Minimum inhibitory concentrations (MICs) for *Haemophilus influenzae* ATCC 33391, *Haemophilus influenzae* ATCC 4927, and *Moraxella catarrhalis* ATCC 25238 were quantified using spiral gradient endpoint assays, as in Example 18.1, except that plates contained GC II agar and were incubated in a 5% $CO_2$/95% air atmosphere.

Example 18.3

Assay of Inhibition of Growth of *Mycobacterium tuberculosis*

MICs for Mycobacterium tuberculosis H37Rv were quantified using microplate Alamar Blue assays as described (Collins, L. & Franzblau, S. (1997) *Agents Chemother.* 41, 1004-1009].

Example 18.4

Assay of Inhibition of Growth of *Bacillus anthracis, Francisella tularensis*, and *Burkholderia mallei*

MICs for *Bacillus anthracis* Vollum 1B, *Francisella tularensis* SCHU4, and Burkholderia mallei CHN7 were quantified using broth microdilution assays as described [Clinical and Laboratory Standar& Institute (CLSUNCCLS) (2009) *Methods for Dilution Antimicrobial Susceptibility Tests for Bacteria That Grow Aerobically; Approved Standard, Eighth Edition. CLIS Document M07-A8* (CLIS, Wayne Pa.)].

TABLE 1

| name | IC50 Ec RNAP (uM) | IC50 Mt RNAP (uM) | IC50 Sa RNAP (uM) | MIC *M. tuberculosis* H37Rv (ug/ml) | MIC *S. aureus* 12600 (ug/ml) | MIC *E. faecalis* 19433 (ug/ml) | MIC *B. anthracis* Vollum-1b (ug/ml) | MIC *E. coli* D21f2tolC (ug/ml) |
|---|---|---|---|---|---|---|---|---|
| 0MTK11 | 3.5 | 2.5 | 11 | >50 | 16 | >40 | 6.25 | 8 |
| 0MTK12 | 2.6 | 4.8 | 9 | 50 | 16 | 32 | 12.5 | 6 |
| 0MTK13 | 1.1 | 2.3 | 4.3 | 25 | 4 | 11 | 6.25 | 2.7 |
| OMTK14 | 2.7 | 9.9 | 7.2 | >50 | >40 | >40 | 25 | 12 |
| OMTK15 | 3 | 3 | 7.2 | 50 | >40 | >40 | 25 | 12 |
| OMTK18 | 2.7 | 3.9 | 7.9 | | >40 | >40 | | 11 |
| OMTK21 | 2.4 | 4.4 | 7.2 | | >40 | >40 | | 10 |
| OMTK22 | 1.3 | 1.7 | 3.7 | | 10 | 22 | | 5 |
| OMTK23 | 1.6 | 2.3 | 4.8 | | 12 | 25 | | 5 |
| 0MTK26 | 1.5 | 3.6 | 5.4 | | 12.5 | 36 | | 6.2 |
| 0MTK27 | 2.3 | 4.9 | 5.4 | | 9.8 | 16 | | 4.3 |
| 0MTK28 | 2.7 | 4.6 | 6.4 | | 6.9 | 11 | | 3 |
| 0MTK30 | 1.8 | 3.7 | 4.1 | | 16 | 26 | | 7 |
| 0MTK31 | 1.9 | 3.5 | 4.8 | | 14 | 22 | | 6 |
| 0MTK32 | 2 | 3.3 | 3.7 | | 3.6 | 6.6 | | 2.2 |
| OMTK33 | 6.2 | 8.3 | | | >40 | >40 | | |

| name | MIC *H. influenzae* 33391 (ug/ml) | MIC *H. influenzae* 49247 (ug/ml) | MIC *M. catarrhalis* 25238 (ug/ml) | MIC *F. tularensis* SCHU4 (ug/ml) | MIC *B. mallei* CHN7 (ug/ml) |
|---|---|---|---|---|---|
| 0MTK11 | >40 | 35 MIC50 | >40 | 3.125 | 50 |
| 0MTK12 | >40 | >40 | >40 | 3.125 | 50 |
| 0MTK13 | 32 | 32 | 32 | 3.125 | 12.5 |
| OMTK14 | >40 | >40 | >40 | 12.5 | >50 |
| OMTK15 | >40 | >40 | >40 | 12.5 | >50 |
| OMTK18 | | | | | |
| OMTK21 | | | | | |
| OMTK22 | | | | | |
| OMTK23 | | | | | |
| 0MTK26 | | | | | |
| 0MTK27 | | | | | |
| 0MTK28 | | | | | |
| 0MTK30 | | | | | |
| 0MTK31 | | | | | |
| 0MTK32 | | | | | |
| OMTK33 | | | | | |

Example 19

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |

| (v) Injection 2 (10 mg/ml) | mg/ml |
|---|---|
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

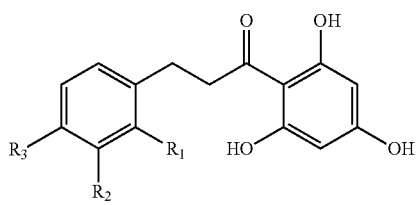

wherein:
R₁ is H, Cl, Br, I, (C₁-C₆)alkyl, optionally substituted by halogen, or (C₁-C₆)alkoxy, optionally substituted by halogen;
R₂ is H, halogen, trifluoromethyl, (C₂-C₆)alkyl, optionally substituted by halogen, or (C₁-C₆)alkoxy, optionally substituted by halogen; and
R₃ is H, halogen, trifluoromethyl, (C₂-C₆)alkyl, optionally substituted by halogen, or (C₂-C₆)alkoxy, optionally substituted by halogen;
provided that at least one of R₁, R₂, or R₃ is not H;
or a salt thereof.

2. The compound of claim 1, which is

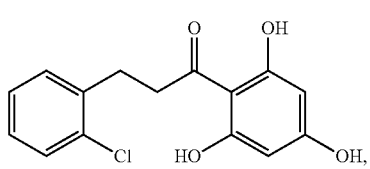
OMTK11

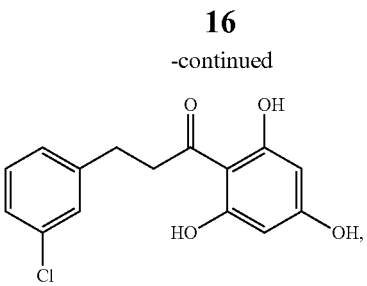
OMTK12

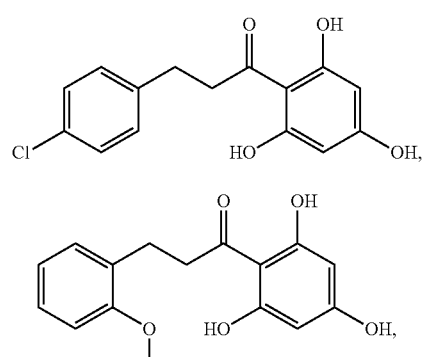
OMTK13

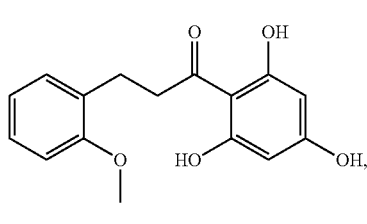
OMTK14

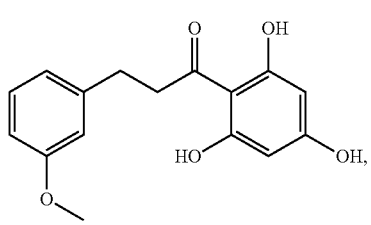
OMTK15

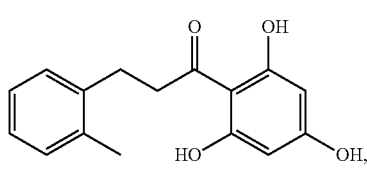
OMTK18

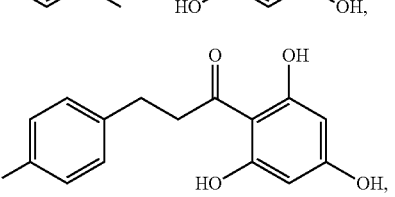
OMTK21

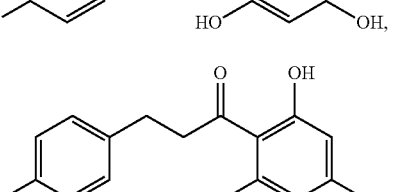
OMTK22

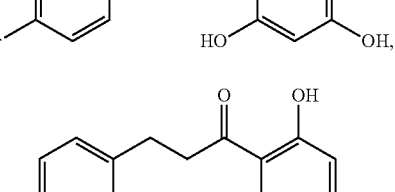
OMTK23

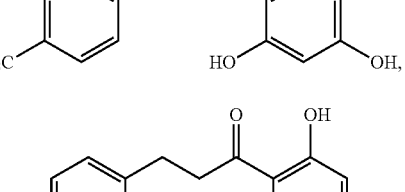
OMTK26

-continued

OMTK27: structure with isopropyl-phenyl-CH2CH2-C(=O)-phenyl(OH)(HO)(OH)

OMTK28: structure with tert-butyl-phenyl-CH2CH2-C(=O)-phenyl(OH)(HO)(OH)

OMTK30: structure with 4-F, 2-methyl phenyl-CH2CH2-C(=O)-phenyl(OH)(HO)(OH)

OMTK31: structure with 2-CF3 phenyl-CH2CH2-C(=O)-phenyl(OH)(HO)(OH), or

OMTK32: structure with 4-CF3, 2-CF3 phenyl-CH2CH2-C(=O)-phenyl(OH)(HO)(OH), or a salt thereof.

3. A composition comprising a compound of formula I as described in claim 1, or a pharmaceutically acceptable salt thereof, and a pharmaceutically acceptable vehicle.

4. A method for inhibiting a bacterial RNA polymerase comprising contacting the bacterial RNA polymerase with a compound of formula I as described in claim 1, or a salt thereof.

5. A method for inhibiting the growth of a bacterium comprising contacting the bacterium with a compound of formula I as described in claim 1, or a salt thereof.

6. A method for treating a bacterial infection selected from *Mycobacterium tuberculosis, Staphylococcus aureus* MSSA and MRSA, *Enterococcus faecalis, Enterococcus faecium, Bacillus anthracis, Escherichia coli, Haemophilus influenzae, Moraxella catarrhalis, Francisella tularensis* or *Burkholderia mallei* in a mammal comprising administering to the mammal an effective amount of a compound of formula I as described in claim 1, or a pharmaceutically acceptable salt thereof.

7. The composition of claim 3, in the form of a disinfectant, sterilant, antispoilant, or antiseptic.

8. A composition comprising a compound of formula I as described in claim 2, or a pharmaceutically acceptable salt thereof, and a pharmaceutically acceptable vehicle.

9. The composition of claim 8, in the form of a disinfectant, sterilant, antispoilant, or antiseptic.

10. A method for treating a bacterial infection selected from *Mycobacterium tuberculosis, Staphylococcus aureus* MSSA and MRSA, *Enterococcus faecalis, Entercoccus faecium, Bacillus anthracis, Escherichia coli, Haemophilus infuenzae, Moraxella catarrhalis, Francisella tularensis* or *Burkholderia mallei* in a mammal comprising administering to the mammal an effective amount of a compound of formula I as described in claim 2, or a pharmaceutically acceptable salt thereof.

11. A method for inhibiting a bacterial RNA polymerase comprising contacting the bacterial RNA polymerase with a compound of formula I as described in claim 2, or a salt thereof.

12. A method for inhibiting the growth of a bacterium comprising contacting the bacterium with a compound of formula I as described in claim 2, or a salt thereof.

13. A compound of formula I:

Formula I: structure with $R_3$, $R_2$, $R_1$ substituted phenyl-CH2CH2-C(=O)-phenyl(OH)(HO)(OH)

wherein:
$R_1$ is H, Cl, Br, I, $(C_1-C_6)$alkyl, optionally substituted by halogen, or $(C_1-C_6)$alkoxy, optionally substituted by halogen;
$R_2$ is H, Cl, Br, I, trifluoromehtyl, $(C_2-C_6)$alkyl, optionally substituted by halogen, or $(C_1-C_6)$alkoxy, optionally substituted by halogen;
$R_3$ is H, halogen, trifluoromethyl, $(C_2-C_6)$alkyl, optionally substituted by halogen, or $(C_2-C_6)$alkoxy, optionally substituted by halogen;
provided that at least one of $R_1$, $R_2$, or $R_3$ is not H;
or a salt thereof.

14. The compound of claim 13, provided that at least one of $R_1$ or $R_3$ is H.

* * * * *